United States Patent
Teles et al.

(10) Patent No.: US 8,212,082 B2
(45) Date of Patent: Jul. 3, 2012

(54) PROCESS FOR THE ISOLATION OF DODECATRIENAL AND ITS USE AS AROMA SUBSTANCE

(75) Inventors: Joaquim Henrique Teles, Otterstadt (DE); Beatrice Rößler-Feigel, Weisenheim am Sand (DE); Alexander Hauk, Ludwigshafen (DE); Christian Müller, Mannheim (DE); Michael Schelper, Ludwigshafen (DE); Tanja Kirchner, Nierstein (DE); Susanne Szeschkus, Alzey (DE)

(73) Assignee: BASF SE, Ludwigshafen (DE)

( * ) Notice: Subject to any disclaimer, the term of this patent is extended or adjusted under 35 U.S.C. 154(b) by 149 days.

(21) Appl. No.: 12/694,851

(22) Filed: Jan. 27, 2010

(65) Prior Publication Data

US 2010/0190869 A1    Jul. 29, 2010

(30) Foreign Application Priority Data

Jan. 28, 2009   (EP) .................................... 09151526

(51) Int. Cl.
- C07C 45/28 (2006.01)
- A61K 8/35 (2006.01)
- A61K 47/08 (2006.01)
- C11D 3/50 (2006.01)

(52) U.S. Cl. ............. 568/365; 568/469.9; 514/772; 512/8; 510/102

(58) Field of Classification Search .......... 568/365, 568/469.9; 514/772; 512/8; 510/102
See application file for complete search history.

(56) References Cited

U.S. PATENT DOCUMENTS

| | | | |
|---|---|---|---|
| 2,875,256 A | 2/1959 | Hyman et al. | |
| 2010/0256398 A1 | 10/2010 | Pinkos et al. | |
| 2011/0269996 A1 | 11/2011 | Teles et al. | |

FOREIGN PATENT DOCUMENTS

| | | |
|---|---|---|
| EP | 0 279 397 | 8/1988 |
| JP | 62 12735 | 1/1987 |
| JP | 62 16412 | 1/1987 |
| WO | WO 2005/030690 | 4/2005 |
| WO | WO 2006/032502 | 3/2006 |
| WO | WO 2007/060160 | 5/2007 |
| WO | WO 2008/000754 | 1/2008 |
| WO | WO2008/000756 A1 * | 1/2008 |
| WO | WO 2008/000757 | 1/2008 |
| WO | WO 2008/071632 | 6/2008 |
| WO | WO 2009/092682 | 7/2009 |
| WO | WO 2009/092683 | 7/2009 |
| WO | WO 2010/023211 | 3/2010 |

OTHER PUBLICATIONS

U.S. Appl. No. 12/674,058.
U.S. Appl. No. 12/674,466.
U.S. Appl. No. 12/694,815.
Starokon et al. "Liquid Phase Oxidation of Alkenes with Nitrous Oxide to Carbonyl Compounds", Advanced Synthesis & Catalysis, Wiley VCH Verlag, Weinheim, Jan. 1, 2004, pp. 268-274.
Blank et al, J. Agric. Food Chem. (2001), 49, pp. 2959-2965.
Ran et al, Tetrahedron Letters 45 (2004), pp. 7851-7853.
Bohlmann et al., Liebigs Ann. Chem. (1982), pp. 1216-1218.
Surbuerg, J. Panten "Common Fragrance and Flavor Materials", Wiley-VCH, 5th Ed., (2006), pp. 15-16.
International Search Report—PCT/EP2010/050887 filed Jan. 27, 2010—mailed Jul. 6, 2010.
English Translation of International Search Report—PCT/EP2010/050887 filed Jan. 27, 2010—mailed Jul. 6, 2010.
International Preliminary Report—PCT/EP2010/050887 filed Jan. 27, 2010—mailed Jul. 6, 2010.

* cited by examiner

Primary Examiner — Sikarl Witherspoon
(74) Attorney, Agent, or Firm — Connolly Bove Lodge & Hutz LLP

(57) ABSTRACT

The present invention relates to a process for preparing at least one compound with Z−1 cycles and 7 to 16 carbon atoms with at least one aldehyde group, at least comprising the stages:
- (a1) oxidation of a composition (A), at least comprising a cyclic olefin with Z cycles and 7 to 16 carbon atoms and at least two C—C double bonds, by means of dinitrogen monoxide to give a composition (A1),
- (a2) separating off the at least one cyclic olefin with Z cycles and 7 to 16 carbon atoms with at least two C—C double bonds from the composition (A1) from stage (a1) in order to obtain a composition (A2),
- (b1) separating off the at least one cyclic compound with Z cycles and 7 to 16 carbon atoms with a keto group from the composition (A2) from step (a2), in order to obtain a composition (B1), comprising at least 50% by weight of the at least one compound with Z−1 cycles and 7 to 16 carbon atoms with at least one aldehyde group and at least two C—C double bonds, where Z may be 1, 2, 3 or 4.

11 Claims, No Drawings

PROCESS FOR THE ISOLATION OF DODECATRIENAL AND ITS USE AS AROMA SUBSTANCE

CROSS REFERENCE TO RELATED APPLICATIONS

This application claims priority to EP 09151526.2 filed Jan. 28, 2009, the entire contents of all are hereby incorporated by reference.

The present invention relates to a process for preparing at least one compound with Z−1 cycles and 7 to 16 carbon atoms with at least one aldehyde group and at least two C—C double bonds, at least comprising the stages:
(a1) oxidation of a composition (A), at least comprising a cyclic olefin with Z cycles and 7 to 16 carbon atoms and at least two C—C double bonds, by means of dinitrogen monoxide to give a composition (A1), at least comprising at least one cyclic compound with Z cycles and 7 to 16 carbon atoms with a keto group, the at least one cyclic olefin with Z cycles and 7 to 16 carbon atoms with at least two C—C double bonds and the at least one compound with Z−1 cycles and 7 to 16 carbon atoms with at least one aldehyde group and at least two C—C double bonds,
(a2) separating off the at least one cyclic olefin with Z cycles and 7 to 16 carbon atoms with at least two C—C double bonds from the composition (A1) from stage (a1) in order to obtain a composition (A2), at least comprising the at least one cyclic compound with Z cycles and 7 to 16 carbon atoms with a keto group and at least one compound with Z−1 cycles and 7 to 16 carbon atoms with at least one aldehyde group and at least two C—C double bonds,
(b1) separating off the at least one cyclic compound with Z cycles and 7 to 16 carbon atoms with a keto group from the composition (A2) from step (a2), in order to obtain a composition (B1), comprising at least 50% by weight of the at least one compound with Z−1 cycles and 7 to 16 carbon atoms with at least one aldehyde group and at least two C—C double bonds,
where Z may be 1, 2, 3 or 4. Furthermore, the present invention relates to a mixture comprising 4,8,11-dodecatrienal and 1,5,9-cyclododectrienes, and also to the use of this mixture as fragrance, for example in perfumes, cosmetics, soaps, cleaning compositions, shampoos, foods, hygiene products or pharmaceuticals.

The use of compounds which have at least one aldehyde group and at least two C—C double bonds as fragrances and/or processes for the preparation of these compounds are already known from the prior art.

The only commercial aldehydes with at least two C—C double bonds which are used as fragrances are given in the next figure, the trade name being given in square brackets (see in this regard H. Surburg, J. Panten, "Common Fragrance and Flavor Materials", 5th ed., Wiley-VCH (2006)).

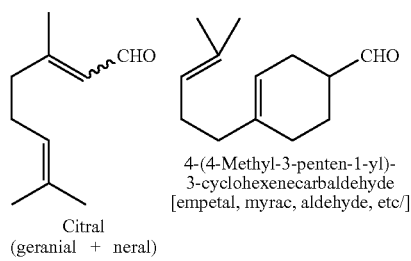

Citral
(geranial + neral)

4-(4-Methyl-3-penten-1-yl)-
3-cyclohexenecarbaldehyde
[empetal, myrac, aldehyde, etc/]

-continued

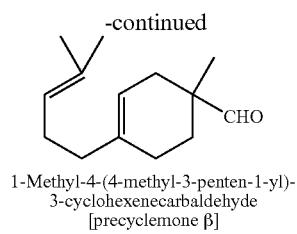

1-Methyl-4-(4-methyl-3-penten-1-yl)-
3-cyclohexenecarbaldehyde
[precyclemone β]

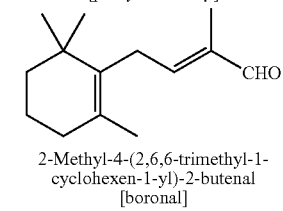

2-Methyl-4-(2,6,6-trimethyl-1-
cyclohexen-1-yl)-2-butenal
[boronal]

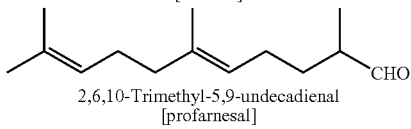

2,6,10-Trimethyl-5,9-undecadienal
[profarnesal]

The Japanese patent applications with the laid-open numbers S62-16412 and S62-12735 disclose a process for preparing 2E,4E-(or 4Z)-2,4,11-dodecatrienal in which 2E-(or 2Z)-decadienal is reacted with the corresponding Wittig reagent to give the diethyl full acetal of the desired product. Acidic hydrolysis of the full acetal produces the corresponding aldehyde.

Blank et al., J. Agric. Food Chem. 2001, 49, 2959-2965 disclose a process for preparing (E,Z,Z)-2,4,7-tridecatrienal by oxidizing arachidonic acid, and the use of this unsaturated aldehyde as fragrance.

Ran et al., Tetrahedron Letters 45 (2004), 7851-7853, disclose a process for preparing 2E,4E,6E-dodecatrienal. This process is based on a regioselective chain extension of 2E,4E-decadienal.

Bohlmann et al., Liebigs Ann. Chem. 1982, pages 1216 to 1218, disclose a process for preparing (2E,4Z)-2,4,1'-dodecatrien-1-al by reacting the corresponding phosphorylide based on 1,7-octadiene with ethyl fumaraldehydate and subsequently reducing the ester function to the aldehyde function.

4,8,11-Dodecatrienals can be synthesized by a targeted synthesis only with difficulty, and no synthesis has hitherto been described in the literature. Linear unsaturated aldehydes are known as valuable fragrances (H. Surburg, J. Panten, "Common Fragrance and Flavor Materials" Wiley-VCH, 5th edition, 2006, pages 15 and 16).

It is therefore an object of the present invention to provide a process with which cyclic or acyclic compounds having 7 to 16 carbon atoms with at least one aldehyde group and at least two C—C double bonds can be obtained in good yield and high purity. It is a further object of the present invention that existing plants and/or apparatuses can be reused for the preparation of cyclic ketones having 7 to 16 carbon atoms in order to keep additional apparatus construction to a minimum.

These objects are achieved according to the invention by a process for preparing a compound with Z−1 cycles and 7 to 16 carbon atoms with at least one aldehyde group and at least two C—C double bonds, at least comprising the stages:
(a1) oxidation of a composition (A), at least comprising a cyclic olefin with Z cycles and 7 to 16 carbon atoms and at least two C—C double bonds, by means of dinitrogen monoxide to give a composition (A1), at least comprising at least one cyclic compound with Z cycles and 7 to 16 carbon atoms with a keto group,
the at least one cyclic olefin with Z cycles and 7 to 16 carbon atoms with at least two C—C double bonds and
the at least one compound with Z-1 cycles and 7 to 16 carbon atoms with at least one aldehyde group and at least two C—C double bonds,
(a2) separating off the at least one cyclic olefin with Z cycles and 7 to 16 carbon atoms with at least two C—C double bonds from the composition (A1) from stage (a1) in order to obtain a composition (A2), at least comprising
at least one cyclic compound with Z cycles and 7 to 16 carbon atoms with a keto group and
the at least one compound with Z-1 cycles and 7 to 16 carbon atoms with at least one aldehyde group and at least two C—C double bonds,
(b1) separating off the at least one cyclic compound with Z cycles and 7 to 16 carbon atoms with a keto group from the composition (A2) from step (a2), in order to obtain a composition (B1), comprising at least 50% by weight of the at least one compound with Z-1 cycles and 7 to 16 carbon atoms with at least one aldehyde group and at least two C—C double bonds,
where Z may be 1, 2, 3 or 4.

Surprisingly, it has been found that especially aldehydes which have one cycle less (Z-1 cycles) than the starting compounds used can be obtained by oxidizing the specified starting materials with dinitrogen monoxide in a high purity and good yield. In one preferred embodiment, the compound with Z-1 cycles and 7 to 16 carbon atoms with at least one aldehyde group which can be prepared by the process according to the invention has one aldehyde group.

By means of the process according to the invention, especially compounds with Z-1 cycles and 7 to 16 carbon atoms and at least one aldehyde group and at least two C—C double bonds can be obtained with a purity of, for example, at least 95%, preferably at least 98%. The purity can be determined by all methods known to the person skilled in the art, for example gas chromatography. A further advantage of the process according to the invention is that it can be easily combined with existing plants, meaning that no costly modifications are required.

The individual stages of the process according to the invention are described in detail below:

Stage (a1)

(a1) oxidation of a composition (A), at least comprising a cyclic olefin with Z cycles and 7 to 16 carbon atoms and at least two C—C double bonds, by means of dinitrogen monoxide to give a composition (A1), at least comprising
at least one cyclic compound with Z cycles and 7 to 16 carbon atoms with a keto group,
the at least one cyclic olefin with Z cycles and 7 to 16 carbon atoms with at least two C—C double bonds and
the at least one compound with Z-1 cycles and 7 to 16 carbon atoms with at least one aldehyde group and at least two C—C double bonds.

The reaction according to stage (a) can generally take place according to all process procedures in which the olefin and dinitrogen monoxide react with one another.

In stage (a1) of the process according to the invention, the cyclic olefin is oxidized through reaction with dinitrogen monoxide. Here, at least one suitable solvent or diluent can be used for the reaction of the cyclic olefin with dinitrogen monoxide. Suitable ones are, inter alia, cyclic alkanes, for example cyclododecane or cyclododecanone or saturated aliphatic or aromatic optionally alkyl-substituted hydrocarbons, with essentially all customary solvents and/or diluents being suitable with the proviso that they have neither a C—C double bond, nor a C—C triple bond, nor an aldehyde group.

In general, the addition of a solvent or diluent is not necessary during the reaction of the cyclic olefin with dinitrogen monoxide.

The temperature during the reaction of the cyclic olefin with dinitrogen monoxide is preferably 140 to 350° C., further preferably 180 to 320° C. and particularly preferably 200 to 300° C.

It is possible to carry out the reaction of the cyclic olefin with dinitrogen monoxide at two or more temperatures or in two or more temperature ranges which are in each case within the limits stated above. Temperature changes in the course of the reaction can be carried out continuously or discontinuously.

The pressure during the reaction of the cyclic olefin with dinitrogen monoxide is preferably higher than the intrinsic pressure of the starting material mixture and/or product mixture at the selected reaction temperature or the selected reaction temperatures. The pressure is preferably 1 to 1000 bar, further preferably 40 to 325 bar and particularly preferably 50 to 200 bar.

It is possible to carry out the reaction of the cyclic olefin with dinitrogen monoxide at two or more pressures or in two or more pressure ranges which are in each case within the limits stated above. Pressure changes in the course of the reaction can be carried out continuously or discontinuously.

There are no particular restrictions regarding the reactors which can be used for the reaction of the cyclic olefin with dinitrogen monoxide. In particular, the reaction can take place in batch mode or in continuous mode. Accordingly, reactors which may be used are, for example, at least one CSTR (Continuous Stirred Tank Reactor) with at least one internal and/or at least one external heat exchanger, at least one tubular reactor, at least one tube-bundle reactor or at least one loop reactor. It is likewise possible to configure at least one of these reactors such that it has at least two different zones. Such zones can differ, for example, in reaction conditions such as, for example, the temperature or the pressure and/or in the geometry of the zone such as, for example, the volume or the cross section. If the reaction is carried out in two or more reactors, it is possible to use two or more identical types of reactor or at least two different types of reactor.

The reaction of the cyclic olefin with dinitrogen monoxide is preferably carried out in a single reactor. For example the reaction is preferably in continuous mode. A suitable reactor is described, for example, in the as yet unpublished patent application EP 09151002.4.

The residence time of the reaction material in the at least one reactor during the reaction of the cyclic olefin with dinitrogen monoxide is generally in the range up to 20 hours, preferably in the range from 0.1 to 20 hours, further preferably in the range from 0.2 to 15 hours and particularly preferably in the range from 0.25 to 10 hours.

In the feed which is fed to the reaction of dinitrogen monoxide with the cyclic olefin, the molar ratio of dinitrogen monoxide and the cyclic olefin is generally in the range from 0.05 to 4, preferably in the range from 0.06 to 1, further preferably in the range from 0.07 to 0.5 and particularly preferably in the range from 0.1 to 0.4.

The reaction of the cyclic olefin with Z cycles and 7 to 16 carbon atoms with at least two C—C double bonds with dinitrogen monoxide can be carried out such that a conversion of the cyclic olefin in the range up to 50%, preferably in the range from 5 to 30% and particularly preferably in the range from 10 to 20% is achieved.

In principle, according to the invention, any cyclic olefin with Z cycles and 7 to 16 carbon atoms with at least two C—C double bonds or any mixture of two or more different cyclic olefins with Z cycles and 7 to 16 carbon atoms with in each case at least two C—C double bonds can be reacted with dinitrogen monoxide.

According to the invention, the formulation "Z cycles" means that the correspondingly described compounds have cyclic units in a number of Z. According to the invention, Z is 1, 2, 3 or 4, for example for the preferred compounds (I) to (VIII) and (XI), Z is 1, for the preferred compounds (IX) and (X), Z is 2. For the particularly preferred case that Z is 1, the process according to the invention thus particularly preferably produces acyclic compounds (Z=1, consequently Z−1=0), i.e. compounds which have no cycle, with 7 to 16 carbon atoms and at least one aldehyde group and at least two C—C double bonds.

Preferably, according to the invention, the cyclic olefin has two, three or four C—C double bonds.

Consequently, according to a further embodiment, the present invention also relates to a process, as described above, for preparing a compound with Z−1 cycles and 7 to 16 carbon atoms with at least one aldehyde group, where the cyclic olefin has three C—C double bonds.

The present invention preferably also relates to the process according to the invention where the at least one cyclic olefin with at least two C—C double bonds is selected from the group consisting of 1,5-cyclooctadiene, 1,5-cyclododecadiene, 1,9-cyclohexadecadiene, 1,8-cyclotetradecadiene, 1,6-cyclodecadiene, 1,6,11-cyclopentadecatriene, 1,5,9-cyclododecatriene, vinylcyclohexene, norbornadiene, ethylidenenorbornene and mixtures thereof. 1,5-Cyclooctadiene, 1,5-cyclododecadiene, 1,9-cyclohexadecadiene, 1,8-cyclotetradecadiene, 1,6-cyclodecadiene, 1,6,11-cyclopentadecatriene, 1,5,9-cyclododecatriene and vinylcyclohexene have one cycle, therefore in these cases Z is one. In the case of norbornadiene and ethylidenenorbornene, Z is two.

1,5-Cyclooctadiene (I), 1,5-cyclododecadiene (II), 1,9-cyclohexadecadiene (III), 1,8-cyclotetradecadiene (IV), 1,6-cyclododecadiene (V), 1,6,11-cyclopentadecatriene (VI), 1,5,9-cyclododecatriene (VII), 1,5,9,13-cyclohexadecatetraene (VIII), norbornadiene (IX), ethylidenenorbornene (X), vinylcyclohexene (XI), where always only one of the possible isomers is shown, are depicted below:

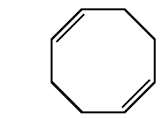

(I)

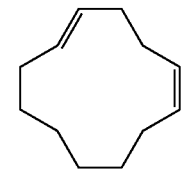

(II)

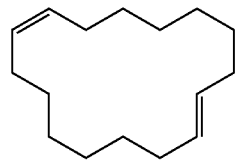

(III)

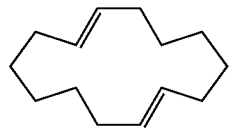

(IV)

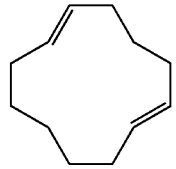

(V)

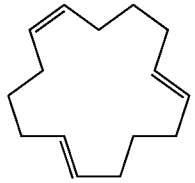

(VI)

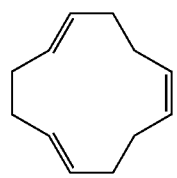

(VII)

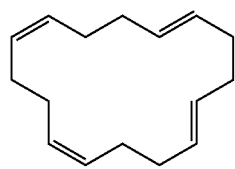

(VIII)

(IX)

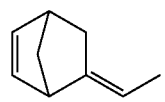

(X)

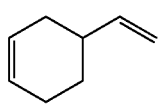

(XI)

The cyclic olefin used is particularly preferably 1,5,9-cyclododecatriene (VII). 1,5,9-Cyclododecatriene can in general be used in any possible isomer, for example cis,trans,trans-1,5,9-cyclododecatriene, cis,cis,trans-1,5,9-cyclododecatriene, all-trans-1,5,9-cyclododecatriene or all-cis-1,5,9-cyclododecatriene, very particularly preferably cis,trans,trans-1,5,9-cyclododecatriene. In the process according to the invention, it is also possible to react a mixture of said isomers and in particular an isomer mixture which comprises predominantly cis,trans,trans-1,5,9-cyclododecatriene.

The present invention therefore relates, in a preferred embodiment, to a process for preparing an aldehyde as described above, where the cyclic olefin with Z cycles and 7 to 16 carbon atoms with at least two double bonds is cyclododecatriene, preferably 1,5,9-cyclododecatriene, particularly preferably cis,trans,trans-1,5,9-cyclododecatriene.

The cyclododecatriene preferably used in the process according to the invention can generally be obtained by all processes known to the person skilled in the art. In one preferred embodiment, the cyclododecatriene is obtained through trimerization of butadiene.

Consequently, according to a further embodiment, the present invention also relates to a process, as described above, for preparing a compound with Z cycles and 7 to 16 carbon atoms with at least one aldehyde group and at least two C—C double bonds, where the cyclic olefin with Z cycles and 7 to 16 carbon atoms with at least two double bonds is 1,5,9-cyclododecatriene which has been prepared from butadiene by means of trimerization.

1,5,9-Cyclododecatriene can be prepared, for example, through trimerization of pure 1,3-butadiene, as is described, for example, in T. Schiffer, G. Oenbrink, "Cyclododecatriene, Cyclooctadiene, and 4-Vinylcyclohexene", in Ullmann's Encyclopedia of Industrial Chemistry, $6^{th}$ Edition (2000), Electronic Release, Wiley VCH, pages 1 to 4. Within the framework of this process, for example in the case of trimerization in the presence of Ziegler catalysts, cis,trans,trans-1,5,9-cyclo-dodecatriene, cis,cis,trans-1,5,9-cyclododecatriene and all-trans-1,5,9-cyclododecatriene are formed, as is described, for example, in H. Weber et al. "Zur Bildungsweise von cis,trans,trans-Cyclododecatrien-(1,5,9) mittels titanhaltiger Katalysatoren [The mode of formation of cis,trans,trans-cyclododecatriene-(1,5,9) by means of titanium-containing catalysts]" in Liebigs Ann. Chem. 681 (1965) pages 10 to 20. Cyclododecatriene can be prepared, for example by trimerization of 1,3-butadiene using a titanium or nickel catalyst, for example in accordance with DE 1283836.

Whereas in principle all suitable titanium catalysts can be used for the trimerization, the titanium tetrachloride/ethylaluminum sesquichloride catalyst described in the article by Weber et al. is particularly suitable.

Whereas in principle all suitable nickel catalysts can be used for the trimerization, the bis-cyclooctadienyl nickel/ethoxydiethyl aluminum catalyst described in DE 1283836 is particularly suitable.

The butadiene used for the trimerization particularly preferably has a degree of purity, determined by gas chromatography, of at least 99.6% and further preferably of at least 99.65%. The 1,3-butadiene used particularly preferably comprises no 1,2-butadiene and no 2-butyne within the detection limits.

This trimerization generally gives mixtures which comprise at least 95% by weight, preferably at least 96% by weight and further preferably at least 97% by weight, of cis,trans,trans-1,5,9-cyclododecatriene. The mixtures particularly preferably comprise about 98% by weight of cis,trans,trans-1,5,9-cyclododecatriene.

This mixture comprising cis,trans,trans-1,5,9-cyclododecatriene can be used as such for the reaction according to the invention according to stage (a1). It is likewise possible to separate off the cis,trans,trans-1,5,9-cyclododecatriene from the mixture by means of at least one suitable method, for example preferably by means of at least one distillation, and use it in the reaction according to stage (a1).

According to a very particularly preferred embodiment of the process according to the invention, the cyclododecatriene used is an isomer mixture which comprises predominantly cis,trans,trans-1,5,9-cyclododecatriene, trans,trans,trans-1,5,9-cyclododecatriene or cis,cis,trans-1,5,9-cyclododecatriene. Preferably, an isomer mixture is used which comprises more than 60% by weight, based on the isomer mixture, of cis,trans,trans-1,5,9-cyclododecatriene, further preferably more than 70% by weight, in particular more than 80% by weight, particularly preferably more than 90% by weight, for example more than 91% by weight, more than 92% by weight, more than 93% by weight, more than 94% by weight, more than 95% by weight, more than 96% by weight, more than 97% by weight or more than 98% by weight.

The olefins which can be used according to the invention can be prepared, for example, by the processes specified in the following literature sources:

(I) cycloocta-1,5-diene is produced as by-product in the synthesis of compound (VII), as is described, for example, in T. Schiffer, G. Oenbrink, "Cyclododecatriene, Cyclooctadiene, and 4-Vinylcyclohexene", in Ullmann's Encyclopedia of Industrial Chemistry, $6^{th}$ Edition (2000), Electronic Release, Wiley VCH.

(II) cyclododeca-1,5-diene can be obtained, for example, by catalytic reduction of compound (VII), as described, for example, in U.S. Pat. No. 3,182,093.

(III) cyclohexadeca-1,9-diene can be obtained by metathesis of cyclooctene, as described, for example in EP 1288181.

(IV) cyclotetradeca-1,8-diene can be obtained by metathesis of cycloheptene, as described, for example, in S. Warwel, H. Kaetker, Synthesis (1987) (10), 935-7.

(V) cyclodeca-1,6-diene, preferably the cis,cis isomer, can be obtained by isomerization of cis,trans-cyclodeca-1,5-diene, as described, for example, in DE 1 230 023.

(VI) cyclopentadecadeca-1,6,11-triene can be obtained by cyclooligomerization of cyclopentene, as described, for example, in DD 115480.

(VII) see (I)

(VIII) cyclohexadeca-1,5,9,13-tetraene can be obtained by tetramerization of butadiene, as described, for example, in U. M. Dzhemilev, L. Yu. Gubaidullin, G. A. Tolstikov, Zhurnal Organicheskoi Khimii (1976), 12(1), 44-6.

(IX) norbornadiene can be obtained by reacting cyclopentadiene with acetylene, as described, for example, in U.S. Pat. No. 2,875,256.

(X) ethylidenenorbornene can be obtained through the base-catalyzed rearrangement of 5-vinyl-2-norbornene, as described, for example, in EP 0 279 397.

(XI) 4-vinylcyclohexene can be prepared by a Diels-Alder reaction of butadiene with itself, but is also produced as a by-product in the preparation of compound (VII), as described, for example, in T. Schiffer, G. Oenbrink, "Cyclododecatriene, Cyclooctadiene, and 4-Vinylcyclohexene", in Ullmann's Encyclopedia of Industrial Chemistry, $6^{th}$ Edition (2000), Electronic Release, Wiley VCH, pages 1-4.

The reaction according to the invention of composition (A), at least comprising one cyclic olefin with Z cycles and 7 to 16 carbon atoms and at least two C—C double bonds, by means of dinitrogen monoxide produces a composition (A1), at least comprising at least one cyclic compound with Z cycles and 7 to 16 carbon atoms with a keto group, the at least one cyclic olefin with Z cycles and 7 to 16 carbon atoms with at least two C—C double bonds and the at least one compound with Z−1 cycles and 7 to 16 carbon atoms with at least one aldehyde group and at least two C—C double bonds.

In general, the preferred reaction according to the invention of cis,trans,trans-1,5,9-cyclododecatriene with dinitrogen monoxide according to stage (a1) results in a cyclododeca-4,8-dienone isomer mixture which comprises at least two of the isomers cis,trans-cyclododeca-4,8-dienone, trans,cis-cyclododeca-4,8-dienone and trans,trans-cyclododeca-4,8-dienone as cyclic compounds with Z cycles and 7 to 16 carbon atoms with a keto group.

Preferably, according to the invention, an isomer mixture is obtained in which trans,cis and cis,trans isomers of this ketone are formed in approximately equal amounts, and the trans,trans isomer is formed in only small amounts compared to the two other isomers. Accordingly, an isomer mixture typical by way of example, has the specified isomers in molar ratios of approximately 1:1:0.08.

The at least one cyclic compound with Z cycles and 7 to 16 carbon atoms with a keto group present in composition (A1) is quantitatively the main product of stage (a1) of the process according to the invention.

Since at least one cyclic compound with Z cycles and 7 to 16 carbon atoms and three double bonds is preferably used as substrate, the preferred product quantitatively formed in stage (a1) of the process according to the invention, through oxidation of one of these double bonds, is at least one cyclic compound with Z cycles and 7 to 16 carbon atoms with two double bonds and one keto group. In one preferred embodiment of the process according to the invention, this cyclic compound with Z cycles and 7 to 16 carbon atoms and a keto group is hydrogenated in a following stage to give at least one saturated cyclic compound with Z cycles and 7 to 16 carbon atoms and a keto group, in particular cyclododecanone.

Within the context of the present invention, the composition (A1) comprises at least one cyclic compound with Z cycles and 7 to 16 carbon atoms with a keto group in an amount of in general more than 5% by weight, preferably more than 10% by weight, preferably 10 to 90% by weight, in particular 11 to 50% by weight, particularly preferably 12 to 40% by weight, especially preferably 13 to 30% by weight, for example 14 to 20% by weight or 15 to 18% by weight.

According to the invention, in composition (A1), at least
  the at least one cyclic olefin with Z cycles and 7 to 16
    carbon atoms with at least two C—C double bonds and
  the at least one compound with Z−1 cycles and 7 to 16
    carbon atoms with at least one aldehyde group and at
    least two C—C double bonds
are also present.

The at least one cyclic olefin with Z cycles and 7 to 16 carbon atoms with at least two C—C double bonds, which is present in composition (A1), is the same compound which has been used as starting compound in composition (A) before the oxidation. The at least one cyclic olefin with Z cycles and 7 to 16 carbon atoms with at least two C—C double bonds in composition (A1) is thus a remaining starting material which has not been oxidized in stage (a1) of the process according to the invention. According to the invention, the at least one cyclic olefin with Z cycles and 7 to 16 carbon atoms with at least two double bonds may be present in composition (A1) in the same isomeric structures in which it has been used as starting material. In one preferred embodiment, in composition (A1), a somewhat different isomer ratio is present with regard to the at least one olefin with Z cycles and 7 to 16 carbon atoms with at least two C—C double bonds than in the starting material used in step (a1). This is accounted for by the different reactivities of the individual isomers, for example the all-trans isomer reacts more rapidly than the cis,trans, trans isomer, and this in turn reacts somewhat more rapidly than the cis,cis,trans isomer.

The desired product of the process according to the invention present in the composition (A1), the at least one compound with Z−1 cycles and 7 to 16 carbon atoms with at least one aldehyde group, is formed in general from the olefin with at least two double bonds used as starting material through oxidative cleavage of a double bond.

Since, as described above, Z describes the number of cycles present in the specified compounds, the formulation "Z−1 cycles" means that in the desired product of the process according to the invention, one cycle fewer is present than in the compounds which comprise Z cycles. According to the invention, the desired product is obtained by a ring-opening reaction and therefore has one cycle fewer than the starting material.

In stage (a1) of the process according to the invention, if appropriate, at least one compound with Z cycles and 7 to 16 carbon atoms with at least one aldehyde group is also formed as by-product. This at least one by-product has the same number of cycles as the starting material used in stage (a1). This at least one compound is preferably a cyclic compound with at least one aldehyde group which is formed by ring contraction. This optionally present by-product thus has the same number of cycles as the starting material.

For the preferred case that 1,5,9-cyclododecatriene, in particular cis,trans,trans-1,5,9-cyclododecatriene (Z=1) is used as the starting material in the process according to the invention, the product desired according to the invention obtained is at least one compound with Z−1 cycles and 7 to 16 carbon atoms with at least one aldehyde group and at least two C—C double bonds, particularly preferably an isomer mixture of acyclic compounds with an aldehyde group and three double bonds, for example a mixture of 4,8,11-dodecatrienals. Particularly preferably, a mixture of isomeric 4,8,11-dodecatrienals is obtained, comprising the cis,trans, trans,cis, trans,trans isomers, for example in the amounts 50% by weight cis,trans, 45% by weight trans,cis and 5% by weight trans,trans. The cis,trans isomer is depicted as compound (XIII)

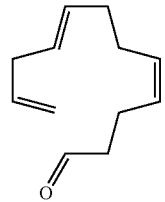

(XIII)

The present invention also relates to the process according to the invention where the at least one compound with Z−1 cycles and 7 to 16 carbon atoms with at least one aldehyde group and at least two C—C double bonds is a 4,8,11-dodecatrienal.

In one preferred embodiment of the process according to the invention, the composition (A1) obtained in stage (a1) additionally comprises at least one cyclic compound with Z cycles and 7 to 16 carbon atoms with at least two keto groups. This compound is formed from the olefin having at least two double bonds used as starting material through oxidation of two of the double bonds present with dinitrogen monoxide.

For the particularly preferred case that in the process according to the invention, the starting material used is 1,5,9-cyclododecatriene, in particular cis,trans,trans-1,5,9-cyclododecatriene, the at least one cyclic compound with Z cycles and 7 to 16 carbon atoms with at least two keto groups obtained is particularly preferably an isomer mixture of cyclic compounds with two keto functions and a double bond, in particular cyclododecenediones, for example a mixture of 8-cis-cyclododecene-1,5-dione, 9-cis-cyclododecene-1,6-dione, 8-cis-cyclododecene-1,4-dione, 8-trans-cyclododecene-1,5-dione, 8-trans-cyclododecene-1,4-dione and 9-trans-cyclododecene-1,6-dione isomers, for example in the approximate ratio of 38:19:19:12:6:6. The 8-cis-cyclododecene-1,5-dione formed as main isomer is depicted as compound (XII)

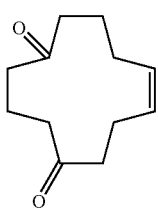

(XII)

Besides the specified desired product, the specified by-products and unreacted starting material, the composition (A1) usually comprises further compounds, in particular organic compounds, for example organic compounds with oxygen-containing groups, for example alcohols, aldehydes or epoxides. In this connection, the organic compounds can in particular have the same number or a different number of carbon atoms as the cyclic aldehyde present in the composition (A1). In the composition (A1), unreacted dinitrogen monoxide and formed nitrogen may be present in addition to the specified components. Consequently, stage (a1) in a particularly preferred embodiment comprises (a1) oxidation of a composition (A), at least comprising a cyclic olefin with Z cycles and 7 to 16 carbon atoms and at least two C—C double bonds, by means of dinitrogen monoxide to give a composition (A1), at least comprising
at least one cyclic compound with Z cycles and 7 to 16 carbon atoms with a keto group,
the at least one cyclic olefin with Z cycles and 7 to 16 carbon atoms with at least two C—C double bonds,
the at least one compound with Z-1 cycles and 7 to 16 carbon atoms with at least one aldehyde group and at least two C—C double bonds and
dinitrogen monoxide and nitrogen.

Within the context of the present invention, in stage (a1), dinitrogen monoxide can be used in pure form or in the form of a gas mixture comprising dinitrogen monoxide.

In principle, in stage (a1) of the process according to the invention, any gas mixture comprising dinitrogen monoxide can be used. According to the invention, it is also possible to purify or concentrate the gas mixture comprising dinitrogen monoxide prior to use in stage (a). A suitable purification process comprises, for example, the absorption of the gas mixture in an organic solvent or water, the desorption of the gas mixture from the laden organic solvent or the laden water and the adjustment of the content of nitrogen oxides NO in the gas mixture to at most 0.01 to 0.001% by volume, based on the total volume of the gas mixture. Such a process is described, for example, in DE 10 2004 046 167.8, the content of which relating to this is incorporated in its entirety into the context of the present application.

Here, the gas mixture comprising dinitrogen monoxide used can in principle originate from any desired source. In particular, it is possible for the dinitrogen monoxide source used to be the off-gas of a process as described in WO 2006/032502, WO 2007/060160 and WO 2008/071632, and in the as yet unpublished applications EP 08153953.8 and EP 08153952.0.

The term "gas mixture", as used within the context of the present invention, refers to a mixture of two or more compounds which are in the gaseous state at ambient pressure and ambient temperature. At altered temperature or altered pressure, the gas mixture may also be present in another state of aggregation, for example liquid, and is still referred to as a gas mixture within the context of the present invention.

According to the invention, a mixture of different off-gases can also be used.

According to a further preferred embodiment of the present invention, the off-gas comprising at least one dinitrogen monoxide originates from an adipic acid plant, a dodecanedioic acid plant, a hydroxylamine plant and/or a nitric acid plant, the latter in turn preferably being operated with at least one off-gas from an adipic acid plant, a dodecanedioic acid plant, a glyoxal plant or a hydroxylamine plant.

According to the invention, the gas mixture can be used in gaseous form. However, it is also possible to firstly treat the gaseous mixture comprising dinitrogen monoxide in such a way that the gas mixture and/or dinitrogen monoxide is present in liquid or supercritical form and is then used. The gas mixture and/or dinitrogen monoxide can be liquefied through suitable selection of the pressure or the temperature. Within the context of the present invention, it is likewise possible to dissolve the gas mixture in a solvent.

The reaction of the at least one cyclic olefin with Z cycles and 7 to 16 carbon atoms and at least two C—C double bonds with dinitrogen monoxide according to step (a1) can in principle take place in the presence of a catalyst, but also without the addition of a catalyst.

After stage (a1), the composition (A1) obtained in stage (a1)) is treated in stage (a2) according to the invention.

In one preferred embodiment, the composition (A1) obtained from stage (a1) is decompressed in a stage (a1b) in order to remove any gaseous starting materials or products still present, for example unreacted $N_2O$ or formed $N_2$, before composition (A1) is used in stage (a2). The decompression can take place by processes known to the person skilled in the art, for example by transferring the composition (A1) to a room in which a lower pressure prevails.

The process according to the invention thus preferably comprises a step (a1b)

(a1b) decompression of the composition (A1) in order to remove dinitrogen monoxide and nitrogen in order to obtain a composition (A1) which is essentially free from dinitrogen monoxide and nitrogen.

Stage (a2):

(a2) separating off the at least one cyclic olefin with Z cycles and 7 to 16 carbon atoms with at least two C—C double bonds from the composition (A1) from stage (a1) in order to obtain a composition (A2), at least comprising
at least one cyclic compound with Z cycles and 7 to 16 carbon atoms with a keto group and
the at least one compound with Z-1 cycles and 7 to 16 carbon atoms with at least one aldehyde group and at least two C—C double bonds.

In stage (a2) of the process according to the invention, starting material of the process according to the invention which has not been reacted in the oxidation reaction in stage (a1) is separated off from the composition (A1) in order to obtain the composition (A2).

Stage (a2) can take place by all methods known to the person skilled in the art. In one preferred embodiment, in stage (a2) of the process according to the invention, a distillation is carried out in order, for example, to separate off unreacted starting material, i.e. at least one cyclic olefin with Z cycles and 7 to 16 carbon atoms with at least two C—C double bonds, from the product stream in order to return this preferably to stage (a1) of the process according to the invention.

In one preferred embodiment, a simple distillation column with packings known to the person skilled in the art is used for the distillation in stage (a2). The distillation in stage (a2) of the process according to the invention is preferably carried out in vacuo, for example at a pressure ≦1000 mbar, preferably ≦500 mbar, particularly preferably ≦300 mbar. For the case preferred according to the invention that the starting material used is an olefinic compound with 12 carbon atoms, stage (a2) is preferably carried out at a pressure of ≦120 mbar, particularly preferably ≦70 mbar, very particularly preferably ≦60 mbar. According to the invention, distillation columns known to the person skilled in the art can be used, preference being given to those which have at least 20, preferably at least 25, particularly preferably at least 30, theoretical plates. In a further preferred embodiment, 35 to 55% of the plates are located in the stripping section of the distillation column. The reflux ratio in the preferred embodiment where an olefinic compound with 12 carbon atoms is used as starting material is 1 to 2, preferably 1.2 to 1.8. For the other specified starting materials, the reflux ratio can be adjusted by the person skilled in the art.

The top product of this distillation obtained is essentially pure starting material, i.e. at least one cyclic olefin with Z cycles and 7 to 16 carbon atoms with at least two C—C double bonds, which, in a particularly preferred embodiment, is recycled as substrate to stage (a1)) of the process according to the invention.

In one preferred embodiment, the present invention relates to the process according to the invention where the at least one cyclic olefin with Z cycles and 7 to 16 carbon atoms with at least two C—C double bonds separated off in stage (a2) is recycled again to stage (a1).

The bottom product obtained in the described distillation in stage (a2) corresponds essentially to the composition (A2) described above.

The product desired according to the invention, the at least one compound with Z-1 cycles and 7 to 16 carbon atoms with at least one aldehyde group and at least two C—C double bonds, is present in the composition (A2) generally in an amount of from 0.1 to 50.0% by weight, preferably 0.5 to 10.0% by weight, particularly preferably 1.0 to 5.0% by weight.

In the preferred embodiment of the process according to the invention where the composition (A1) also comprises at least one cyclic compound with Z cycles and 7 to 16 carbon atoms and at least two keto groups, in stage (a2) of the process according to the invention, a composition (A2) is obtained, at least comprising the at least one cyclic compound with Z cycles and 7 to 16 carbon atoms with a keto group and
the at least one compound with Z-1 cycles and 7 to 16 carbon atoms with at least one aldehyde group and at least two C—C double bonds and
at least one cyclic compound with Z cycles and 7 to 16 carbon atoms with at least two keto groups.

In one preferred embodiment, the at least one cyclic compound with Z cycles and 7 to 16 carbon atoms with at least two keto groups is present in the composition (A2) in general in an amount of from 0.1 to 20.0% by weight, preferably 0.5 to 10.0% by weight, particularly preferably 1.0 to 5.0% by weight.

In a further embodiment of the process according to the invention, stage (a2) can also be carried out such that the desired product, the at least one compound with Z-1 cycles and 7 to 16 carbon atoms with at least one aldehyde group, is obtained in the distillation column described above as side take-off. Here, the starting material to be separated off in this step, i.e. the at least one olefin with Z cycles and 7 to 16 carbon atoms and at least two C—C double bonds, remains the top product of stage (a1). In this case, the at least one compound with Z-1 cycles and 7 to 16 carbon atoms with at least one aldehyde group and at least two C—C double bonds obtained as side take-off additionally comprises starting material unreacted in stage (a1), i.e. at least one cyclic olefin with Z cycles and 7 to 16 carbon atoms and at least two C—C double bonds, for example in an amount of from 0.1 to 5% by weight, preferably 1 to 3% by weight. In a preferred embodiment, the fraction obtained as side take-off can be used directly in stage (b2) in order to obtain the desired product in a purity required for fragrances.

Stage (b1):

Stage (b1) of the process according to the invention comprises (b1) separating off the at least one cyclic compound with Z cycles and 7 to 16 carbon atoms with a keto group from the composition (A2) from step (a2), in order to obtain a composition (B1), comprising at least 50% by weight of the at least one compound with Z-1 cycles and 7 to 16 carbon atoms with at least one aldehyde group and at least two C—C double bonds.

The separating off of the at least one cyclic compound with Z cycles and 7 to 16 carbon atoms with a keto group in step (b1) of the process according to the invention can generally take place by all processes suitable and known to the person skilled in the art. In a particularly preferred embodiment, the separating off in step (b1) of the process according to the invention takes place by distillation.

In one preferred embodiment, stage (b1) of the process according to the invention is carried out in at least two columns. In one particularly preferred embodiment, composition (A2) from step (a2) is treated in a first step in a simple distillation column (T1). This gives preferably a top stream (K1), which consists essentially of at least one compound with Z-1 cycles and 7 to 16 carbon atoms with at least one aldehyde group and at least two C—C double bonds, and comprises, if appropriate, at most 35% by weight, preferably at most 30% by weight, particularly preferably at most 25% by weight, of at least one cyclic compound with Z cycles and 7 to 16 carbon atoms with a keto group. Furthermore, a bottom stream (S1) is obtained which can comprise all residual components, including the at least one compound with Z cycles and 7 to 16 carbon atoms and a keto group and the at least one cyclic compound with Z cycles and 7 to 16 carbon atoms with at least two keto groups.

As distillation column (T1) it is possible to use all columns known to be suitable to the person skilled in the art. In one preferred embodiment, the column (T1) comprises at least 15 theoretical plates, particularly preferably at least 20. In this connection, it is further preferred that most of the plates, for example at least 50% of the plates, are in the rectifying section of the column. The distillation in the distillation column (T1) is preferably carried out at a pressure below atmospheric pressure, for example, particularly for the preferred case where the starting material used is an olefinic compound with 12 carbon atoms, at a top pressure of less than 50 mbar, particularly preferably less than 20 mbar. For the other compounds which can be used according to the invention, a suitable pressure can be ascertained by the person skilled in the art. The distillation in the distillation column (T1) is carried out for the preferred case where the starting material used is an olefinic compound with 12 carbon atoms preferably at a bottom temperature of from 120 to 220° C., particularly preferably 150 to 200° C. For the other starting materials suitable according to the invention, the distillation temperature, also depending on the established pressure, can be selected by the person skilled in the art.

Preferably, the bottom stream (S1) from the first distillation column (T1) is treated in at least one further simple distillation column (T2). In one preferred embodiment in this connection, a top stream (K2) is obtained which comprises essentially at least one cyclic compound with Z cycles and 7 to 16 carbon atoms with at least one keto group. In one preferred embodiment, this top stream (K2) comprises essentially no compound with Z−1 cycles and 7 to 16 carbon atoms with at least one aldehyde group and at least two C—C double bonds, i.e. less than 1.0% by weight, in a preferred embodiment at most 0.2% by weight. In the second distillation in T2 of the process according to the invention (step (b1)), a bottom stream (S2) is furthermore obtained which comprises at least one cyclic compound with Z cycles and 7 to 16 carbon atoms with at least two keto groups and other by-products of the oxidation according to step (a1), but comprises at most 40% by weight, preferably at most 25% by weight, of the at least one cyclic compound with Z cycles and 7 to 16 carbon atoms with a keto group.

As distillation column (T2) it is possible to use any column which is known to be suitable to the person skilled in the art. In one preferred embodiment, the column has at least 30 plates, particularly preferably at least 35 plates. In a further preferred embodiment, most of the plates are in the stripping section, particularly preferably at least 28 theoretical plates are in the stripping section. The distillation in separating column (T2) preferably takes place at a pressure below atmospheric pressure, for the preferred case where an olefinic compound with 12 carbon atoms is used as starting material, for example at a top pressure of ≦50 mbar, particularly preferably ≦25 mbar. The distillation in the distillation column (T2) is carried out, for the preferred case where an olefinic compound with 12 carbon atoms is used, preferably at a bottom temperature of from 120 to 220° C., particularly preferably 150 to 200° C. For the other starting materials suitable according to the invention, the temperature, also depending on the established pressure, can be easily adjusted by the person skilled in the art.

According to the invention, it is also possible to operate the distillation columns (T1) and (T2) in reverse order, i.e. to separate in the first column the at least one cyclic compound with Z cycles and 7 to 16 carbon atoms with at least one keto group and the at least one compound with Z−1 cycles and 7 to 16 carbon atoms with at least one aldehyde group and at least two C—C double bonds overhead, and in the second column to separate off the at least one cyclic compound with Z−1 cycles and 7 to 16 carbon atoms with at least one aldehyde group and at least two C—C double bonds overhead.

The preferably used columns (T1) and (T2) are described, for example, in Olujic et al., Chem. Biochem. Eng. Q. 2003, 17, pages 301 to 309. In a further preferred embodiment of step (b1) of the process according to the invention, the columns (T1) and (T2) are thermally coupled together, for example by using a side column without its own evaporator and condenser (Petlyuk arrangement).

Very particularly preferably, instead of the two distillation columns (T1) and (T2) in step (b1) of the process according to the invention, a single dividing wall column is used.

According to the invention, any dividing wall column which appears to be suitable to the person skilled in the art for the present separation problem can be used in step (b1) of the process according to the invention. Suitable dividing wall columns are given in Olujic et al., Chem. Biochem. Eng. Q. 2003, 17, pages 301 to 309.

In one preferred embodiment, a continuous dividing wall column is used, which preferably has at least three zones. The dividing wall column preferably has a lower zone, which has preferably at least 2, particularly preferably at least 4, theoretical trays. Furthermore, the preferably used dividing wall column has a middle section, which preferably has at least 15, particularly preferably at least 25, theoretical trays. In a further preferred embodiment, the dividing wall column used has an upper section, which preferably has at least 4, particularly preferably at least 7, theoretical trays. The middle section is subdivided into an inlet section and an outlet section by a dividing wall which is preferably arranged in the middle.

In a further preferred embodiment, the dividing wall column is equipped with a suitable packing. Suitable column packings are known to the person skilled in the art, for example from J. F. Fair in "Handbook of Separation Process Technology", R. W. Rousseau (ed.), (1987), John Wiley & Sons, pages 295-312.

In order to keep the temperature during the distillation in the dividing wall column as low as possible, a pressure below atmospheric pressure is preferably used, for example a pressure within the dividing wall column of less than 500 mbar, preferably less than 200 mbar, in particular less than 100 mbar and very particularly preferably less than 50 mbar. The pressure difference between column bottom and column top is preferably less than 50 mbar. In one preferred embodiment, the top pressure in the dividing wall column is 0.1 to 100 mbar, particularly preferably 3 to 50 bar.

In the dividing wall column, the distillation is carried out preferably at a bottom temperature of from 150 to 220° C., particularly preferably 160 to 200° C. These values apply in particular for the preferred case where an olefinic compound with 12 carbon atoms is used as starting material, for the other starting materials which can be used according to the invention, the values can be adjusted accordingly by the person skilled in the art.

The low-boiling components of the composition (B1) are preferably separated off as top stream (K3) at the top of the dividing wall column. In general, the top stream (K3) comprises the desired product of the process according to the invention, i.e. at least one compound with Z−1 cycles and 7 to 16 carbon atoms with at least one aldehyde group and at least two C—C double bonds. The top stream (K3) generally comprises at least 50% by weight, particularly preferably at least 70% by weight, very particularly preferably at least 75% by weight, of at least one compound with Z−1 cycles and 7 to 16 carbon atoms and at least one aldehyde group and at least two C—C double bonds. In addition to the desired product, top stream (K3) can also comprise at least one cyclic olefin with Z cycles and 7 to 16 carbon atoms and at least two C—C bonds, i.e. starting material unreacted in step (a1), and if appropriate at most 35% by weight, preferably at most 30% by weight, particularly preferably at most 25% by weight, of at least one cyclic compound with Z cycles and 7 to 16 carbon atoms with a keto group.

As bottom product of the dividing wall column, the high-boiling components of the composition (A2) are preferably separated off as bottom stream (S2). In one preferred embodiment, bottom stream (S2) comprises at least one cyclic compound with Z cycles and 7 to 16 carbon atoms with at least two keto groups and other by-products of the oxidation according to step (a1). (S2) generally comprises at most 40% by weight, preferably at most 25% by weight, of the at least one cyclic compound with Z cycles and 7 to 16 carbon atoms with a keto group.

Via the side take-off of the dividing wall column, a composition is obtained which comprises essentially at least one cyclic compound with Z cycles and 7 to 16 carbon atoms with a keto group. Furthermore, if appropriate at least one cyclic compound with Z cycles and 7 to 16 carbon atoms with at least two keto groups and at least one compound with Z−1 cycles and 7 to 16 carbon atoms with at least one aldehyde group and at least two C—C double bonds may be present in this composition. The distillation is preferably carried out such that the amount of these two secondary components in the side take-off is minimized. Specifically, the distillation is carried out such that in the side take-off less than 0.5% by weight of the at least one cyclic compound with Z cycles and 7 to 16 carbon atoms with at least two keto groups and less than 1% by weight of the at least one compound with Z–1 cycles and 7 to 16 carbon atoms with at least one aldehyde group and at least two C—C double bonds are present.

The top stream (K3), which comprises essentially the desired product, at least one compound with Z–1 cycles with 7 to 16 carbon atoms with at least one aldehyde group and at least two C—C double bonds, can additionally comprise starting material unreacted in stage (a1), i.e. at least one cyclic olefin with Z cycles and 7 to 16 carbon atoms and at least two C—C double bonds, for example in an amount of from 0.1 to 20% by weight, preferably 1 to 15% by weight. For the use of the product according to the invention as fragrance, a content of at least one cyclic olefin with Z cycles and 7 to 16 carbon atoms with at least two C—C double bonds of from 0 to 5% by weight, preferably 0 to 1% by weight, particularly preferably 0 to 0.1% by weight, very particularly preferably 0 to 0.05% by weight, is generally required. Consequently, the product obtained according to the invention as top stream (K3) is purified in a subsequent step in a preferred embodiment.

In a preferred embodiment, the present invention also relates to the process according to the invention where the at least one cyclic compound with Z cycles and 7 to 16 carbon atoms with a keto group separated off in step (b1) has at least one C—C double bond.

In a further preferred embodiment, the present invention also relates to the process according to the invention where the at least one cyclic compound with Z cycles and 7 to 16 carbon atoms with a keto group is hydrogenated with at least one C—C double bond according to step (b1) to give at least one saturated cyclic compound with Z cycles and 7 to 16 carbon atoms with a keto group. Corresponding hydrogenation processes are known to the person skilled in the art.

Consequently, in one preferred embodiment, the present invention relates to the process according to the invention where the following step (b2) follows step (b1):
(b2) purification of the composition (B1) obtained in step (b1) in order to obtain a mixture which comprises at least 92% by weight of the at least one compound with Z–1 cycles and 7 to 16 carbon atoms with at least one aldehyde group and at least two C—C double bonds.

The purification in the optional step (b2) of the process according to the invention can take place by all processes known to the person skilled in the art. In one preferred embodiment, the purification in step (B2) takes place by a distillation. This distillation can be carried out continuously or discontinuously, i.e. in a batch process. Preferably, the distillation in step (b2) is carried out in a batch process.

In a particularly preferred embodiment, stage (b2) of the process according to the invention is carried out in a distillation boiler which has an attached column on top. The column particularly preferably has at least 20 plates. In a further preferred embodiment, the distillation is carried out in stage (b2) of the process according to the invention at reduced pressure, i.e. at a pressure below atmospheric pressure. For the preferred case where an olefin with 12 carbon atoms is used in the process according to the invention, this distillation is carried out at a top pressure of from 0.1 to 100 mbar, very particularly preferably 3 to 50 mbar. For the other starting materials which can be used according to the invention, the distillation pressure has to be adjusted accordingly by the person skilled in the art. When the distillation is carried out in a batch process, in general firstly fractions are obtained which still comprise at least one cyclic olefin with Z cycles with 7 to 16 carbon atoms and at least two C—C double bonds. Afterwards, fractions are obtained which comprise the desired product in the corresponding purity.

After stage (b2) of the process according to the invention, a mixture is obtained which comprises in general 92 to 99.8% by weight, preferably 94 to 99.5% by weight, particularly preferably 95 to 99.2% by weight, very particularly preferably 96 to 99% by weight, of the at least one compound with Z–1 cycles and 7 to 16 carbon atoms with at least one aldehyde group and at least two C—C double bonds, preferably at least one 4,8,11-dodecatrienal, and 0.0001 to 5% by weight, preferably 0.001 to 2% by weight, particularly preferably 0.01 to 0.5% by weight, very particularly preferably 0.05 to 0.4% by weight, of the at least one cyclic olefin with Z cycles and 7 to 16 carbon atoms and at least two C—C double bonds, preferably at least one 1,5,9-cyclododecatriene. As the remainder up to 100% by weight, further unidentifiable compounds are also present in the mixture in small amounts, for example up to 2% by weight. The sum of the amounts of the compound with Z–1 cycles and 7 to 16 carbon atoms with at least one aldehyde group and at least two C—C double bonds, of the at least one cyclic olefin with Z cycles and 7 to 16 carbon atoms and at least two C—C double bonds and of the further unidentifiable compounds, i.e. by-products originating from the process according to the invention, is in each case 100% by weight. The sum of the amounts of the individual components does not exceed 100% by weight. The compositions can be determined by processes known to the person skilled in the art, for example gas chromatography.

The present invention also relates to a mixture comprising 92 to 99.8% by weight, preferably 94 to 99.5% by weight, particularly preferably 95 to 99.2% by weight, very particularly preferably 96 to 99% by weight, of the at least one cyclic compound with Z–1 cycles and 7 to 16 carbon atoms with at least one aldehyde group and at least two C—C double bonds and 0.0001 to 5% by weight, preferably 0.001 to 2% by weight, particularly preferably 0.01 to 0.5% by weight, very particularly preferably 0.05 to 0.4% by weight, of the at least one cyclic olefin with Z cycles and 7 to 16 carbon atoms and at least two C—C double bonds. As regards the sum of the amounts of the present components, that stated above is applicable.

The present invention preferably relates to a mixture comprising 92 to 99.8% by weight, preferably 94 to 99.5% by weight, particularly preferably 95 to 99.2% by weight, very particularly preferably 96 to 99% by weight, of at least one 4,8,11-dodecatrienal and 0.0001 to 5% by weight, preferably 0.001 to 2% by weight, particularly preferably 0.01 to 0.5% by weight, very particularly preferably 0.05 to 0.4% by weight, of 1,5,9-cyclododecatrienes. As regards the sum of the amounts of the present components, that stated above is applicable.

The mixture according to the invention particularly preferably comprises 40 to 50% by weight of (E,Z)-4,8,11-dodecatrienal, 40 to 50% by weight of (Z,E)-4,8,11-dodecatrienal, 0.1 to 10% by weight of (E,E)-4,8,11-dodecatrienal and 0.0001 to 5% by weight of 1,5,9-cyclododecatrienes. As regards the sum of the amounts of the present components, that stated above is applicable.

The mixture prepared according to the invention is suitable as fragrance. The mixture prepared according to the invention has the scent of fir needles and wood.

The present invention therefore also relates to the use of the mixture according to the invention as fragrance, for example in perfumes, cosmetics, soaps, cleaning compositions, shampoos, foods, hygiene products or pharmaceuticals.

The mixture according to the invention is present for the applications according to the invention in customary amounts, for example 0.0001 to 5% by weight. It is possible that the mixture according to the invention is present alone as fragrance. Moreover, it is also possible for the mixture according to the invention to be used in a mixture with further fragrances and/or further additives known to the person skilled in the art, for example stabilizers, emulsifiers, surfactants or dyes.

The at least one cyclic compound with Z cycles and 7 to 16 carbon atoms with a keto group separated off in stage (b1) according to the invention can, if appropriate, be further treated by processes known to the person skilled in the art, for example hydrogenation, treatment with bases, Brønstedt acids and/or Lewis acids, distillative treatment. Suitable processes are described, for example in WO 2008/000757 A1, WO 2008/000756 A1 WO 2005/030690 A2 and WO 2008/000754 A1.

The present invention is illustrated in more detail below by reference to examples.

EXAMPLES

Example 1

Oxidation of 1,5,9-cyclododecatriene (CDT) with $N_2O$ 2000 g/h of 1,5,9-cyclododecatriene and 68 g/h of liquid $N_2O$ are pumped from corresponding storage containers and by means of suitable dosing pumps via a static mixer into a tubular reactor (jacketed tube, wound, Ø inside=6 mm, length 36 m). The tube is thermostated to 280° C. by means of heat-transfer oil, which flows in the jacket co-currently to the product, the oil outlet temperature being less than 2° C. above the oil inlet temperature. The reaction pressure is regulated to 100 bar at the reactor outlet by means of a pressure regulating valve. The conversion of 1,5,9-cyclododecatriene at the reactor outlet is 11.3%. After passing the reaction zone, the reaction mixture is decompressed in two uninsulated flash containers firstly to 3 bar and then to 60 mbar in order to take away the formed $N_2$ and unreacted $N_2O$. In so doing, the product cools to below 100° C. The liquid product is then distilled in a packed column with at least 7 theoretical plates at 60 mbar (T(bottom)=170° C., T(top)=130° C.). The top product obtained is unreacted 1,5,9-cyclododecatriene with a purity of >99%, which is recycled to the reaction again. The bottom discharge is an only slightly yellowish liquid and has the composition listed in Table 1, determined by gas chromatography.

TABLE 1

| Compound | Amount [% by wt.] |
|---|---|
| Cyclododeca-4,8-dienones | 92.0 |
| 4,8,11-Dodecatrienals | 2.3 |
| Cyclododecenediones | 2.2 |
| Cyclododecenediones | 2.2 |
| Cycloundeca-3,7-dienecarbaldehyde | 1.0 |
| 1,5,9-Cyclododecatriene | 0.4 |
| trans-1,2-Epoxy-cis,trans-5,9-cyclododecadiene | 0.01 |
| Dimers | 2.0 |
| Others, unidentified | Remainder to 100 |

The product is collected and used in Example 2.

Example 2

Isolation of 4,8,11-Dodecatrienal as Raw Material

For the distillation of the product mixture from Example 1, a continuous laboratory dividing wall column with an internal diameter of 64 mm and a length of 2.6 m (by which is meant the overall length of the packing) is used. In preliminary experiments with test mixtures, it is ascertained that the column has 35 theoretical plates. The column is divided into three zones. The lower zone (plates 1 to 9) has a length of 0.65 m. The middle zone (plates 9 to 27) is 1.3 m in length and is divided into an inlet side and an outlet side by a dividing wall which is arranged in the middle. On the inlet side, the feed is attached at the height of plate 19. On the outlet side, the side stream product is removed in gaseous form at the height of plate 12. The upper zone (plates 27 to 35) has a length of 0.65 m. The overall column is equipped with a packing (Montz A3 750). The distillation is carried out at a top pressure of ca. 44 mbar, the pressure loss over the packing is 3.6 mbar. In order to minimize the residence time and thus the thermal stress in the bottom, the bottom evaporator used is a Sambay evaporator ("wiped film evaporator"). The top temperature is 137° C. and the bottom temperature 185° C. Using a metering pump, 501 g/h of the mixture to be distilled are metered, the mixture being heated beforehand to 180° C. Via the side stream, 481 g/h of product are obtained which has the composition listed in Table 2, determined by gas chromatography.

TABLE 2

| Compound | Amount [% by wt.] |
|---|---|
| Cyclododeca-4,8-dienones | 98.5 |
| 4,8,11-Dodecatrienals | 0.1 |
| Cyclododecenediones | 0.2 |
| Cycloundeca-3,7-dienecarbaldehyde | 1.1 |
| trans-1,2-Epoxy-cis,trans-5,9-cyclododecadiene | 0.01 |
| Others, unidentified | Remainder to 100 |

This is a colorless liquid with a melting point +1° C.

At the bottom of the distillation, 6 g/h of bottom product are obtained as dark yellow to brown liquid with the composition listed in Table 3, determined by gas chromatography.

TABLE 3

| Compound | Amount [% by wt.] |
|---|---|
| Cyclododeca-4,8-dienones | 6.7 |
| Cyclododecenediones | 47.0 |
| High boilers | 46.0 |
| Others, unidentified | Remainder to 100 |

At the top, 14 g/h of top product are obtained as a colorless liquid with the composition listed in Table 4, determined by gas chromatography.

TABLE 4

| Compound | Amount [% by wt.] |
|---|---|
| 4,8,11-Dodecatrienals | 76.0 |
| Cyclododeca-4,8-dienones | 9.9 |
| 1,5,9-Cyclododecatriene | 13.6 |
| Others, unidentified | Remainder to 100 |

The stated flows are average values from a continuous distillation during which a total of 80 kg of feed are processed.

The side-stream product can then, for example, be further processed to give cyclododecanone according to WO 2005/030690 or WO 2008/000754.

The top product is already highly enriched in 4,8,11-dodecatrienals. The 4,8,11-dodecatrienal present here further consists of a mixture of three isomers which are still present in the same ratio as in the product mixture from Example 1.

Example 3

Purification of 4,8,11-Dodecatrienal by Distillation 770 g of the top product from Example 2 (with the composition stated therein) are rectified in an automated batch distillation plant at reduced pressure. The plant comprises a column with a diameter of 30 mm and a height of 3.5 m, which is filled with a packing (Sulzer DX, total length: 3.17 m). The distillation is carried out at a constant top pressure of 40 mbar and the pressure difference between top and bottom of the distillation column is ca. 5 mbar. The reflux ratio is adjusted at the start (until the first 100 g have distilled over) to 100. At this time, the reflux ratio is increased to 150. Always about 25 g are distilled and before a new fraction is taken (at the start or whenever the conditions are rapidly changed even smaller fractions are collected). The four fractions between 217 and 317 g of distillate all have virtually the same composition and all distill at a top temperature between 138.8 and 144.0° C. The four fractions (colorless liquid) comprise 98.2% by weight of the desired 4,8,11-dodecatrienals as ca. 1:1 mixture of the cis,trans and trans,cis isomers (the trans,trans isomer has a higher boiling point and remains in the bottom). As impurities, also 0.26% by weight of 1,5,9-cyclododecatriene and 0.06% by weight of 4,8-cyclododecadienone, besides further unidentified secondary components, are present.

Example 4

Odor Experiment 1 ml of the product from Example 3 is poured into a freshly rinsed screw-lid glass with a volume of 370 ml (diameter 70 mm) and the glass is closed with a factory-new screw lid made of plastic. The closed glass is then left to stand for 15 minutes at room temperature. For smelling, the glass is briefly opened following the equilibration and assessed in terms of odor by the perfumer. The odor impression is described as intensely reminiscent of fir needles, woody and aldehydic smelling.

The invention claimed is:
1. A process for preparing at least one compound with Z-1 cycles and 7 to 16 carbon atoms with at least one aldehyde group, at least comprising the stages:
(a1) oxidation of a composition (A), at least comprising a cyclic olefin with Z cycles and 7 to 16 carbon atoms with at least two C—C double bonds, by means of dinitrogen monoxide to give a composition (A1), at least comprising
at least one cyclic compound with Z cycles and 7 to 16 carbon atoms with a keto group,
the at least one cyclic olefin with Z cycles and 7 to 16 carbon atoms with at least two C—C double bonds and
the at least one compound with Z-1 cycles and 7 to 16 carbon atoms with at least one aldehyde group and at least two C—C double bonds,
(a2) separating off the at least one cyclic olefin with Z cycles and 7 to 16 carbon atoms with at least two C—C double bonds from the composition (A1) from stage (a1) in order to obtain a composition (A2), at least comprising
the at least one cyclic compound with Z cycles and 7 to 16 carbon atoms with a keto group and
at least one compound with Z-1 cycles and 7 to 16 carbon atoms with at least one aldehyde group and at least two C—C double bonds,
(b1) separating off the at least one cyclic compound with Z cycles and 7 to 16 carbon atoms with a keto group from the composition (A2) from step (a2), in order to obtain a composition (B1), comprising at least 50% by weight of the at least one compound with Z-1 cycles and 7 to 16 carbon atoms with at least one aldehyde group and at least two C—C double bonds,
where Z may be 1, 2, 3 or 4, and
(b2) purification of the composition (B1) obtained in step (b1) in order to obtain a mixture which comprises at least 92% by weight of the at least one compound with Z-1 cycles and 7 to 16 carbon atoms with at least one aldehyde group and at least two C—C double bonds.

2. The process according to claim 1, wherein the at least one cyclic olefin with Z cycles and 7 to 16 carbon atoms with at least two C—C double bonds separated off in stage (a2) is recycled again to stage (a1).

3. The process according to claim 1, wherein the at least one cyclic compound with Z cycles and 7 to 16 carbon atoms with a keto group separated off in step (b1) has at least one C—C double bond.

4. The process according to claim 3, wherein the at least one cyclic compound with Z cycles and 7 to 16 carbon atoms with a keto group with at least one C—C double bond is hydrogenated after step (b1) to give at least one saturated cyclic compound with Z cycles and 7 to 16 carbon atoms, with a keto group.

5. The process according to claim 1, wherein the separation in step (b1) takes place by distillation.

6. The process according to claim 1, wherein the at least one cyclic olefin with at least two C—C double bonds is selected from the group consisting of 1,5-cyclooctadiene, 1,5-cyclododecadiene, 1,9-cyclohexadecadiene, 1,8-cyclotetradecadiene, 1,6-cyclodecadiene, 1,6,11-cyclopentadecatriene, 1,5,9-cyclododecatriene, vinylcyclohexene, norbornadiene, ethylidenenorbornene and mixtures thereof.

7. The process according to claim 5, wherein the cyclic olefin is 1,5,9-cyclododecatriene which has been prepared from butadiene by means of trimerization.

8. The process according to claim 1, wherein the at least one compound with Z-1 cycles and 7 to 16 carbon atoms with at least one aldehyde group is 4,8,11-dodecatrienal.

9. A mixture comprising 92 to 99.8% by weight of at least one 4,8,11-dodecatrienal and 0.0001 to 5% by weight of 1,5,9-cyclododecatrienes.

10. The mixture according to claim 9, which comprises 40 to 50% by weight of (E,Z)-4,8,11-dodecatrienal, 40 to 50% by weight of (Z,E)-4,8,11-dodecatrienal, 0.1 to 10% by weight of (E,E)-4,8,11-dodecatrienal and 0 to 1% by weight of 1,5,9-cyclododecatrienes.

11. A method of using a mixture according to claim 9 as fragrance comprising adding the mixture to perfumes, cosmetics, soaps, cleaning compositions, shampoos, foods, hygiene products or pharmaceuticals.

* * * * *